US012582386B2

(12) United States Patent
Amar et al.

(10) Patent No.: US 12,582,386 B2
(45) Date of Patent: Mar. 24, 2026

(54) DIFFERENTIAL PREDICTION OF ABERRATION CORRECTIONS FOR ULTRASOUND THERAPY

(71) Applicant: INSIGHTEC, LTD., Tirat Carmel (IL)

(72) Inventors: Talia Amar, Tirat Carmel (IL); Yoav Levy, Hinanit (IL)

(73) Assignee: INSIGHTEC LTD., Tirat Carmel (IL)

( * ) Notice: Subject to any disclaimer, the term of this patent is extended or adjusted under 35 U.S.C. 154(b) by 258 days.

(21) Appl. No.: 17/909,139

(22) PCT Filed: Mar. 4, 2021

(86) PCT No.: PCT/IB2021/000120
§ 371 (c)(1),
(2) Date: Sep. 2, 2022

(87) PCT Pub. No.: WO2021/176275
PCT Pub. Date: Sep. 10, 2021

(65) Prior Publication Data
US 2023/0100912 A1 Mar. 30, 2023

Related U.S. Application Data

(60) Provisional application No. 62/985,587, filed on Mar. 5, 2020.

(51) Int. Cl.
*A61B 8/00* (2006.01)
*A61N 7/00* (2006.01)

(52) U.S. Cl.
CPC ................. *A61B 8/54* (2013.01); *A61N 7/00* (2013.01); *A61N 2007/0052* (2013.01)

(58) Field of Classification Search
CPC ........... A61B 8/54; A61B 8/08; A61B 8/4461; A61B 8/4488; A61B 8/481; A61N 7/00;
(Continued)

(56) References Cited

U.S. PATENT DOCUMENTS

| | | | |
|---|---|---|---|
| 6,666,833 B1 | 12/2003 | Friedman et al. | |
| 11,291,430 B2 | 4/2022 | Levy et al. | |

(Continued)

FOREIGN PATENT DOCUMENTS

| | | |
|---|---|---|
| JP | 2019-524221 A | 9/2019 |
| WO | 20180020315 | 1/2018 |

(Continued)

OTHER PUBLICATIONS

International Search Report and the Written Opinion, dated Jun. 14, 2021, for the corresponding International Patent Application No. PCT/IB2021/000120, 14 pages.
(Continued)

*Primary Examiner* — Bo Joseph Peng

(74) *Attorney, Agent, or Firm* — MORGAN, LEWIS & BOCKIUS LLP

(57) ABSTRACT

Various approaches for delivering ultrasound energy to a target region during a therapeutic or diagnostic procedure includes implementing an adjustment mechanism having a machine-learning model that has been trained, based on input vectors corresponding to a difference and/or a ratio of parameter values between multiple transducer elements, to generate, for each of the transducer elements, one or more parameter value to compensate for expected beam aberration resulting for an intervening tissue; and activating the transducer elements in accordance with the corresponding parameter values so as to generate an optimized focal zone at the target region during the therapeutic or diagnostic procedure.

34 Claims, 6 Drawing Sheets

(58) Field of Classification Search
    CPC .... A61N 2007/0052; A61N 2007/0078; A61N
             2007/0095; A61N 7/02; G06N 3/044;
             G06N 5/01; G06N 5/02
    See application file for complete search history.

(56)              References Cited

U.S. PATENT DOCUMENTS

| | | | |
|---|---|---|---|
| 2014/0135681 A1* | 5/2014 | Angelsen ................. | A61N 7/00 |
| | | | 604/22 |
| 2017/0140753 A1* | 5/2017 | Jaitly ...................... | G10L 15/16 |
| 2019/0307427 A1 | 10/2019 | Levy et al. | |
| 2019/0336107 A1* | 11/2019 | Hope Simpson ... | G01S 15/8977 |
| 2020/0131025 A1* | 4/2020 | Sinha ..................... | G06N 3/044 |
| 2023/0100912 A1* | 3/2023 | Amar ..................... | G06N 3/044 |
| | | | 600/439 |

FOREIGN PATENT DOCUMENTS

| | | | |
|---|---|---|---|
| WO | WO-2018011631 A2 * | 1/2018 | ........... A61B 6/5217 |
| WO | 20190234495 | 12/2019 | |

OTHER PUBLICATIONS

Office Action issued in the corresponding Japanese Application No.
2022-552555 dated Aug. 18, 2023, with English Translation.

\* cited by examiner

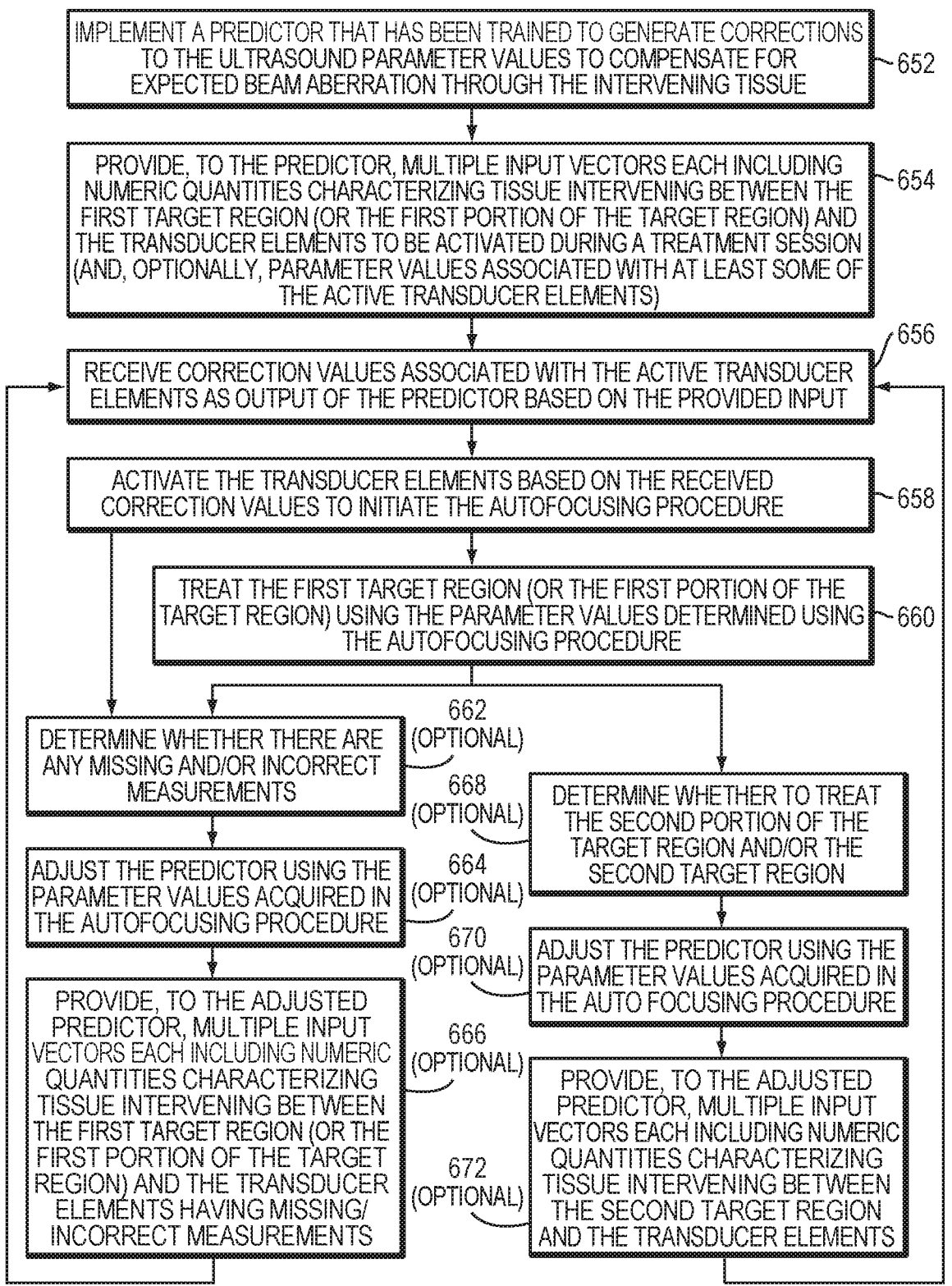

IMPLEMENT A PREDICTOR THAT HAS BEEN TRAINED TO GENERATE CORRECTIONS TO THE ULTRASOUND PARAMETER VALUES TO COMPENSATE FOR EXPECTED BEAM ABERRATION THROUGH THE INTERVENING TISSUE ~652

PROVIDE, TO THE PREDICTOR, MULTIPLE INPUT VECTORS EACH INCLUDING NUMERIC QUANTITIES CHARACTERIZING TISSUE INTERVENING BETWEEN THE FIRST TARGET REGION (OR THE FIRST PORTION OF THE TARGET REGION) AND THE TRANSDUCER ELEMENTS TO BE ACTIVATED DURING A TREATMENT SESSION (AND, OPTIONALLY, PARAMETER VALUES ASSOCIATED WITH AT LEAST SOME OF THE ACTIVE TRANSDUCER ELEMENTS) ~654

RECEIVE CORRECTION VALUES ASSOCIATED WITH THE ACTIVE TRANSDUCER ELEMENTS AS OUTPUT OF THE PREDICTOR BASED ON THE PROVIDED INPUT /656

ACTIVATE THE TRANSDUCER ELEMENTS BASED ON THE RECEIVED CORRECTION VALUES TO INITIATE THE AUTOFOCUSING PROCEDURE ~658

TREAT THE FIRST TARGET REGION (OR THE FIRST PORTION OF THE TARGET REGION) USING THE PARAMETER VALUES DETERMINED USING THE AUTOFOCUSING PROCEDURE ~660

662 (OPTIONAL)

DETERMINE WHETHER THERE ARE ANY MISSING AND/OR INCORRECT MEASUREMENTS 668 (OPTIONAL)

DETERMINE WHETHER TO TREAT THE SECOND PORTION OF THE TARGET REGION AND/OR THE SECOND TARGET REGION 664 (OPTIONAL)

ADJUST THE PREDICTOR USING THE PARAMETER VALUES ACQUIRED IN THE AUTOFOCUSING PROCEDURE 670 (OPTIONAL)

ADJUST THE PREDICTOR USING THE PARAMETER VALUES ACQUIRED IN THE AUTO FOCUSING PROCEDURE 666 (OPTIONAL)

PROVIDE, TO THE ADJUSTED PREDICTOR, MULTIPLE INPUT VECTORS EACH INCLUDING NUMERIC QUANTITIES CHARACTERIZING TISSUE INTERVENING BETWEEN THE FIRST TARGET REGION (OR THE FIRST PORTION OF THE TARGET REGION) AND THE TRANSDUCER ELEMENTS HAVING MISSING/ INCORRECT MEASUREMENTS 672 (OPTIONAL)

PROVIDE, TO THE ADJUSTED PREDICTOR, MULTIPLE INPUT VECTORS EACH INCLUDING NUMERIC QUANTITIES CHARACTERIZING TISSUE INTERVENING BETWEEN THE SECOND TARGET REGION AND THE TRANSDUCER ELEMENTS

FIG. 6B

DIFFERENTIAL PREDICTION OF ABERRATION CORRECTIONS FOR ULTRASOUND THERAPY

CROSS-REFERENCE TO RELATED APPLICATION

This application is a United States National Stage Application filed under 35 U.S.C. § 371 of PCT Patent Application Serial No. PCT/IB2021/000120, filed on Mar. 4, 2021, which claims priority to and the benefits of, U.S. Provisional Patent Application No. 62/985,587, which was filed on Mar. 5, 2020, each of which is hereby incorporated by reference in its entirety.

FIELD OF THE INVENTION

The present invention relates, in general, to ultrasound therapy, and, in particular, to systems and methods for correcting aberrations affecting delivery of ultrasound therapy.

BACKGROUND

Tissue, such as a benign or malignant tumor, organ, or other body region may be treated invasively by surgically removing the tissue, or with minimal intrusion or fully non-invasively by using, for example, thermal ablation. Both approaches may effectively treat certain localized conditions, but involve delicate procedures to avoid destroying or damaging otherwise healthy tissue.

Thermal ablation, as may be accomplished using focused ultrasound, has particular appeal for treating diseased tissue surrounded by or neighboring healthy tissue or organs because the effects of ultrasound energy can be confined to a well-defined target region. Ultrasonic energy may be focused to a zone having a cross-section of only a few millimeters due to relatively short wavelengths (e.g., as small as 1.5 millimeters (mm) in cross-section at one Megahertz (1 MHz)). Moreover, because acoustic energy generally penetrates well through soft tissues, intervening anatomy often does not impose an obstacle to defining a desired focal zone. Thus, ultrasonic energy may be focused at a small target in order to ablate diseased tissue while minimizing damage to surrounding healthy tissue.

To focus ultrasonic energy at a desired target, drive signals may be sent to an acoustic transducer having a number of transducer elements such that constructive interference occurs at the focal zone. At the target, sufficient acoustic intensity may be delivered to heat tissue until necrosis occurs, i.e., until the tissue is destroyed. Preferably, non-target tissue along the path through which the acoustic energy passes (the "pass zone") outside the focal zone is exposed to low-intensity acoustic beams and thus will be heated only minimally, if at all, thereby minimizing damage to tissue outside the focal zone.

The noninvasive nature of ultrasound surgery is particularly appealing for the treatment of brain tumors. However, treatment challenges arising from the anatomy of the human skull have limited the clinical realization of ultrasound therapy. Impediments to transcranial ultrasound procedures include strong attenuation and the distortions caused by irregularities in the skull's shape, density, and sound speed, which contribute toward destroying the ultrasound focus and/or decreasing the ability to spatially register diagnostic image information.

Accordingly, solutions have been proposed to adjust for the effects of ultrasonic energy absorbed by the non-target tissue. In one representative approach, described in U.S. Patent Publication No. 2020/0085409 (the entire disclosure of which is hereby incorporated by reference), a patient-specific 3D skull replica is created and situated in an environment similar to that used to treat the patient; a detector device (e.g., a hydrophone) may be deployed within the skull replica at the target region to measure acoustic signals from each of the ultrasound transducer elements during a simulated treatment sequence. By analyzing the measured signals, corrections to ultrasound parameters (e.g., amplitudes and/or phase shifts) associated with each transducer element may be determined. During treatment, the ultrasound transducer elements may be activated in accordance with the corrected ultrasound parameters so as to compensate for beam aberrations caused by the skull; this may thereby generate a high-quality focus at the target region and/or improve ultrasound beam shaping. Minimizing the area of the focal zone increases the peak acoustic intensity at the target region, and also allows the ultrasound beams transmitted from the transducer elements to be shaped in order to avoid or minimize exposure of the non-target tissue to the therapeutic energy. Creating a 3D skull replica involves cost and time, however, leading practitioners to pursue alternative techniques for correcting beam aberrations caused by patient-specific anatomic features.

One such technique utilizes machine learning. A predictor applicable across patients may be developed based on optimal focusing configurations identified for many specific patients, and which are used as a training set. The trained predictor may estimate optimal corrections to amplitude, phase and/or time delay for all of the transducer elements used for a treatment procedure.

An impediment to the use of machine learning to predict optimal phase and/or amplitude settings is measurement bias, a general term used herein to describe a variety of errors that have a common source, but which might be different for different measurements. By "error" is meant deviation from optimal reference settings rather than measurement inaccuracies. One of these errors may be a constant bias term. Suppose, for example, that an effort is made to predict an optimal focusing configuration with regression, e.g., using an equation such as:

$$\hat{\varphi} = \theta_0 + \theta_1 x_1 + \ldots + \theta_n x_n$$

where $\hat{\varphi}$ is the predicted phase, $\{x_1, x_2 \ldots x_n\}$ is a vector of features and the $\theta$ values are weights; it is essential to know the bias, $\theta_0$, to obtain a prediction, but it may be impossible to accurately estimate this value for a particular measurement in the training set without, for example, accurate knowledge of the water and tissue temperatures, which may be achieved by creating a skull replica as described above. Another possible error arises from and is specific to the location of each transducer element relative to the target (stemming from, e.g., inaccurate knowledge of the exact transducer location in space or to inhomogeneous water and skull temperatures or inaccurate knowledge of the target location), so that different transducer elements contributing to a measurement also contribute different error values. Other errors may arise from input features provided to the predictor, e.g., due to image filters used to process computed tomography (CT) scans. The input vector is typically skull characteristics and/or images of the medium that the elements pass through on the way to the target. Other errors may arise from using data measured at different ultrasound frequencies.

As in any machine-learning exercise, valid training data is critical to development of a predictor for optimal focusing. The measurement errors described above impede the creation of a training dataset that is composed of many different measurements from many different patients, ex-vivo skulls and/or skull replicas, yet which is consistent and learnable. Accordingly, a need exists for mitigating or eliminating inaccuracies in the predicted transducer settings resulting from measurement errors, enabling the effective use of machine learning to provide a high-quality focus at a target region.

SUMMARY

The present invention provides systems and methods for focusing ultrasound beams that traverse tissue (such as a human skull) having an irregular structure, shape, density, and/or thickness onto a target region with a high-quality focus. For ease of reference, the following description only refers to an ultrasound treatment procedure; it should be understood, however, that the same approaches generally apply as well to an ultrasound imaging procedure. In addition, although the description herein refers to ultrasound beams traversing a human skull, the approach described in connection with various embodiments may be applied to determine beam aberrations resulting from any part of the human body, such as ribs, thereby allowing the parameter values characterizing an acoustic beam (e.g., phase shifts and/or amplitudes) to be adjusted to compensate for the aberrations.

Approaches described herein advantageously mitigate or eliminate measurement errors having a common source but potentially affecting different transducer elements differently, so that different measurements may exhibit different errors in the measured parameter(s), e.g., phase, amplitude and/or time delay. In various embodiments, instead of predicting the parameter directly for each transducer element, the predicted value is a relationship between elements, e.g., pairs of elements. The measurement error due to the input (arising from, e.g., the type of imaging and image processing used to characterize intervening tissue) is reduced when the predicted value is a relation (e.g., a difference or a ratio) between values associated with elements having the same source of input, and the measurement error arising from different element locations is reduced by adding constraints on the distance between a plurality (e.g., a pair) of elements; in particular, the bias term in the prediction cancels out when the relation is a difference or a ratio between parameter predictions for the selected elements—for example, in the case of element pairs, what is predicted is the relation in the values of the desired parameter for both elements of each pair (rather than the actual value for each individual element).

In the case of amplitude prediction, the measurements are biased by a multiplicative factor, which is cancelled out when a ratio is taken. In the case of phase prediction, the measurements are biased by an additive factor. Assuming that the bias term is associated mainly with different homogeneous water temperatures, equal element-target distances ensure that the bias term is cancelled out, and if the differences in those distances are much smaller than the mean element-target distance, the term becomes negligible:

$$(\varphi_{el1\_skull}^{T2}-\varphi_{el1\_water}^{T1})-(\varphi_{el2\_skull}^{T2}-\varphi_{el2\_water}^{T1})=$$
$$(\varphi_{el1\_skull}^{T2}-\varphi_{el1\_water}^{T2})-(\varphi_{el2\_skull}^{T2}-$$
$$\varphi_{el2\_water}^{T2})+\varphi_{\Delta d\_water}^{T2}-\varphi_{\Delta d\_water}^{T1}$$

where $\varphi_{elj\_skull}^{Ti}$ denotes a phase shift measured by element j at a temperature $T_i$ in the skull medium; $\varphi_{elj\_water}^{Ti}$ denotes a phase shift measured by element j at a temperature $T_i$ in the water medium; $\varphi_{\Delta d\_water}^{Ti}$ water denotes a phase shift resulting from $\Delta d$, the element-target distance defined as $\Delta d=|target-el_1|-|target-el_2|$, at a temperature $T_i$ in the water medium. For example, in a representative therapy system, the distance between a transducer element and its natural focus distance is 150 mm, and typical brain targeting is several mm from the natural focus (so $\Delta d$ would be at most twice as much). A temperature range of 15°-25° equates to a variation in ultrasound velocity of ~2.5% in water. Therefore, the error caused by this temperature change will be reduced from 2.5% of 150 mm (~1.6$\lambda$ for a 650-kHz transducer) to 2.5% of several mm (<0.1$\lambda$).

For phase shift, the predicted difference represents the difference between the elements' phase shifts that can result in constructive interference at the focal point. All differences refer to the same focal point; if pairs of elements were considered independently rather than as an ensemble, focusing would not be obtained for the entire system. It is the combination of all differences that produces accurate corrections to each transducer element, due in part to the forced inclusion of redundancies in the inference stage (i.e., the same element should appear in multiple pairs). These redundancies produce an overdetermined system of equations that may be analyzed as an optimization problem. A constant bias affecting all elements in the transducer has no effect on the focusing quality, nor on the focus location. Therefore, a selected element may be assigned a reference phase and a conventional optimization algorithm then used to combine the phase differences into a table specifying a phase correction for each element. Biases due to measurement location or inhomogeneous temperature might produce small offsets in focus location; these may be corrected or ignored if clinically insignificant. As used herein, "clinically insignificant" means having an undesired (and sometimes the lack of a desired) effect on tissue that is considered insignificant by clinicians, e.g., prior to the onset of damage thereto or other clinically adverse effect, whether temporary or permanent.

One embodiment uses features corresponding to two sets of skull characteristics (e.g., thickness, density, angle) taken from CT images (or any other skull-imaging technique), each set being associated with a different transducer element; as a result, instead of having a k-length vector as an input for single-element phase shift prediction, a 2 k-length vector is utilized. Another option is to use two sets of CT patches of the skull medium per element combined, for example, in a fourth dimension. Still another option is using a Siamese network, each component of which receives an input corresponding to a single element, and whose overall output is based on a comparison of the component outputs. Other embodiments utilize, for each element pair, a single patch corresponding to the difference in the elements' CT patches. It is possible to utilize groups consisting of more than two elements, in which case the features would be a combination of skull characteristics relative to each element.

The output of the predictor—element-specific adjustments (or corrections) to an ultrasound parameter such as amplitude and/or phase—may be stored in a data structure such as a table that relates parameter values to associated transducer elements for generating an optimal focus at the target. As used herein, the term "optimal" generally involves a substantial improvement (e.g., by more than 10%, more than 20%, or more than 30%) over that obtained using prior-art approaches, but does not necessarily mean that the best theoretically possible focusing properties are achieved.

Accordingly, various embodiments of the present invention advantageously mitigate or eliminate various measurement errors so as to more accurately predict the optimal settings (e.g., phases and/or amplitudes) associated with the transducer elements to account for the effects (e.g., defocusing, mismatching of the acoustic coupling, etc.) of intervening tissue on acoustic energy application to target tissue. In one embodiment, the transducer adjustments made according to predictions are dynamically updated during treatment so as to ensure treatment efficiency during the ultrasound procedure.

Accordingly, in one aspect, the invention pertains to a system for delivering ultrasound energy to a target region during a therapeutic or diagnostic procedure. In various embodiments, the system includes an ultrasound transducer having multiple transducer elements, at least some of which are designated as active during the therapeutic or diagnostic procedure; an adjustment mechanism including a machine-learning model that has been trained on input vectors corresponding to a difference and/or a ratio of parameter values between multiple transducer elements. The adjustment mechanism is configured (i) to receive numeric quantities (e.g., tissue density and/or thickness) characterizing tissue intervening between the active transducer elements and the target region and (ii) based thereon, to generate, for each of the active transducer elements, one or more parameter values to compensate for expected beam aberration. A controller is configured to activate the active transducer elements in accordance with the corresponding parameter values so as to generate an optimized focal zone at the target region during the therapeutic or diagnostic procedure. In one implementation, the generated parameter value(s) specifies a correction to an amplitude, a phase, a frequency, a duty cycle, a sonication pattern and/or a time delay.

The machine-learning model may be a neural network. In addition, the neural network may be trained on input vectors each having parameters associated with a pair of the transducer elements. In one embodiment, the adjustment mechanism includes a lookup table of adjustment values generated by a machine-learning algorithm. The machine-learning algorithm is a neural network trained on input vectors each having parameters associated with more than two transducer elements. In some embodiments, the adjustment mechanism is further configured to generate the parameter value(s) based at least in part on one or more geometric parameters associated with the associated transducer element. The geometric parameter(s) may be, for example, an angle with respect to a surface of a skull between the associated transducer element and the target region. In some embodiments, the difference and/or ratio of ultrasound parameter values are acquired using autofocusing treatment measurements or measurements on ex-vivo or replica skulls.

In some embodiments, the target region includes multiple portions and the generated optimized focal zone is at the first portion of the target region; the controller is further configured to predict (i) a real-time temperature at the second portion, different from the first portion, of the target region, or a non-target region, (ii) a real-time temperature at the focal zone, (iii) a focal spot shape, and/or (iv) treatment success using a physical model. In addition, the controller may be further configured to cause the active transducer elements to (i) transmit ultrasound waves to the target region and (ii) measure reflections of the ultrasound waves from the target region; based on the measurements, classify each of the active transducer elements as a measuring transducer element or a non-measuring transducer element; and update the adjustment mechanism based at least in part on the measurements provided by the measuring transducer elements.

In one embodiment, the updated adjustment mechanism is configured (i) to receive numeric quantities characterizing tissue intervening between the non-measuring transducer elements and the target region and (ii) based thereon, to generate, for each of the non-measuring transducer elements, one or more updated parameter values to compensate for expected beam aberration. The controller is then further configured to activate the non-measuring transducer elements in accordance with the corresponding updated parameter values.

In various embodiments, the controller is further configured to cause the active transducer elements to (i) transmit ultrasound waves to the target region and (ii) measure reflections of the ultrasound waves from the target region; and update the adjustment mechanism based at least in part on the measurements. The updated adjustment mechanism may be configured (i) to receive numeric quantities characterizing tissue intervening between the active transducer elements and the secondary target region, different from the target region, and (ii) based thereon, to generate, for each of the active transducer elements, one or more updated parameter values to compensate for expected beam aberration. The controller is then further configured to activate the active transducer elements in accordance with the corresponding updated parameter values so as to generate an optimized focal zone at the secondary target region.

In another aspect, the invention relates to a method of generating correction values for delivery of ultrasound energy through intervening tissue by an ultrasound transducer including multiple transducer elements, the correction values correcting for beam aberration. In various embodiments, the method includes the steps of training a machine-learning model based on received input vectors, each including (i) a difference and/or a ratio of ultrasound parameters between multiple transducer elements and (ii) numeric quantities (e.g., tissue density and/or thickness) characterizing tissue intervening between multiple transducer elements and a target region, and to generate, as output, correction values of the ultrasound parameters to compensate for expected beam aberration through the intervening tissue. The training may include causing the machine-learning model to learn a relationship between values of the input vectors and corresponding correction values. Multiple input vectors, each having numeric quantities characterizing tissue of the patient intervening between multiple transducer elements to be activated and a target region of the patient, are provided to the machine-learning model. Correction values of the ultrasound parameters are received as output of the machine-learning model based on the provided input vectors. The method may further include activating the transducer elements in accordance with the corresponding correction values of the parameter values so as to generate an optimized focal zone at the target region. In one implementation, the correction values specify corrections to an amplitude, a phase, a frequency, a duty cycle, a sonication pattern and/or a time delay.

The machine-learning model may be a neural network. In addition, the neural network may be trained on input vectors each having parameters associated with a pair of the transducer elements. In some embodiments, the difference and/or ratio of ultrasound parameters are acquired using autofocusing treatment measurements or measurements on ex-vivo or replica skulls. In various embodiments, the input vectors further include one or more geometric parameters associated with each of the transducer elements; the machine-learning model is further trained to generate the correction values of the ultrasound parameters based at least in part on the geometric parameters. The geometric parameter may include, for example, an angle with respect to a surface of a skull between each of the transducer elements and the target region.

In various embodiments, the target region includes multiple portions and the generated optimized focal zone is at the first portion of the target region. The method further includes predicting (i) a real-time temperature at the second portion, different from the first portion, of the target region, or a non-target region, (ii) a real-time temperature at the focal zone, (iii) a focal spot shape, and/or (iv) treatment success using a physical model. In addition, the method may further include activating at least some of the transducer elements to (i) transmit ultrasound waves to the target region and (ii) measure reflections of the ultrasound waves from the target region; based on the measurements, classifying each of the transducer elements as a measuring transducer element or a non-measuring transducer element; and updating the machine-learning model based at least in part on the measurements provided by the measuring transducer elements. In one embodiment, the method further includes providing, to the updated machine-learning model, numeric quantities characterizing tissue intervening between the non-measuring transducer elements and the target region; and receiving, for each of the non-measuring transducer elements, one or more updated parameter values to compensate for expected beam aberration. In addition, the method may further include activating the non-measuring transducer elements in accordance with the corresponding updated parameter values.

In some embodiments, the method further includes activating at least some of the transducer elements to (i) transmit ultrasound waves to the target region and (ii) measure reflections of the ultrasound waves from the target region; and updating the machine-learning model based at least in part on the measurements. In addition, the method may further include providing, to the updated machine-learning model, numeric quantities characterizing tissue intervening between the transducer elements and the secondary target region, different from the target region; and receiving, for each of the transducer elements, at least one updated parameter value to compensate for expected beam aberration. In one embodiment, the method further includes activating the transducer elements in accordance with the corresponding updated parameter values so as to generate an optimized focal zone at the secondary target region.

Another aspect of the invention relates to a method of delivering ultrasound energy through intervening tissue by an ultrasound transducer having multiple transducer elements using a machine-learning model that has been trained with input vectors, each having (i) a difference and/or a ratio of ultrasound parameters between multiple transducer elements and (ii) numeric quantities (e.g., tissue density and/or thickness) characterizing tissue intervening between the transducer elements and a target region, and to generate, as output, correction values of ultrasound parameters to compensate for expected beam aberration through the intervening tissue, the training including causing the machine-learning model to learn a relationship between values of the input vectors and corresponding correction values. In various embodiments, the method includes the steps of providing, to the machine-learning model, multiple input vectors, each having numeric quantities characterizing tissue of the patient intervening between multiple transducer elements to be activated and a target region of the patient; and treating the patient by activating the transducer elements to deliver ultrasound energy according to correction values generated by the machine-learning model based on the provided input vectors so as to generate an optimized focal zone at the target region. In one implementation, the correction values specify corrections to an amplitude, a phase, a frequency, a duty cycle, a sonication pattern and/or a time delay.

The machine-learning model may be a neural network. In addition, the neural network may be trained on input vectors each having parameters associated with a pair of the transducer elements. In some embodiments, the input vectors further comprise one or more geometric parameters associated with each of the transducer elements; the machine-learning model is further trained to generate the correction values of the ultrasound parameters based at least in part on the geometric parameters. The geometric parameter may be, for example, an angle with respect to a surface of a skull between each of the transducer elements and the target region. In one embodiment, the difference and/or ratio of ultrasound parameters are acquired using autofocusing treatment measurements or measurements on ex-vivo or replica skulls.

In various embodiments, the target region includes multiple portions and the generated optimized focal zone is at the first portion of the target region. The method further includes predicting (i) a real-time temperature at the second portion, different from the first portion, of the target region, or a non-target region, (ii) a real-time temperature at the focal zone, (iii) a focal spot shape, and/or (iv) treatment success using a physical model. In addition, the method may further include activating at least some of the transducer elements to (i) transmit ultrasound waves to the target region and (ii) measure reflections of the ultrasound waves from the target region; based on the measurements, classifying each of the transducer elements as a measuring transducer element or a non-measuring transducer element; and updating the machine-learning model based at least in part on the measurements provided by the measuring transducer elements. In one embodiment, the method further includes providing, to the updated machine-learning model, numeric quantities characterizing tissue intervening between the non-measuring transducer elements and the target region; and receiving, for each of the non-measuring transducer elements, one or more updated parameter values to compensate for expected beam aberration. The method may further include activating the non-measuring transducer elements in accordance with the corresponding updated parameter values.

In some embodiments, the method further includes activating at least some of the transducer elements to (i) transmit ultrasound waves to the target region and (ii) measure reflections of the ultrasound waves from the target region; and updating the machine-learning model based at least in part on the measurements. In addition, the method may further include providing, to the updated machine-learning model, numeric quantities characterizing tissue intervening between the transducer elements and a secondary target region, different from the target region; and receiving, for each of the transducer elements, one or more updated parameter values to compensate for expected beam aberration. Further, the method may include activating the transducer elements in accordance with the corresponding updated parameter values so as to generate an optimized focal zone at the secondary target region.

As used herein, the term "substantially" means±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIG. 6B is a flow chart illustrating an exemplary approach for delivering ultrasound energy to a target region during a therapeutic or diagnostic procedure in accordance with various embodiments of the present invention.

DESCRIPTION

Figure 1:
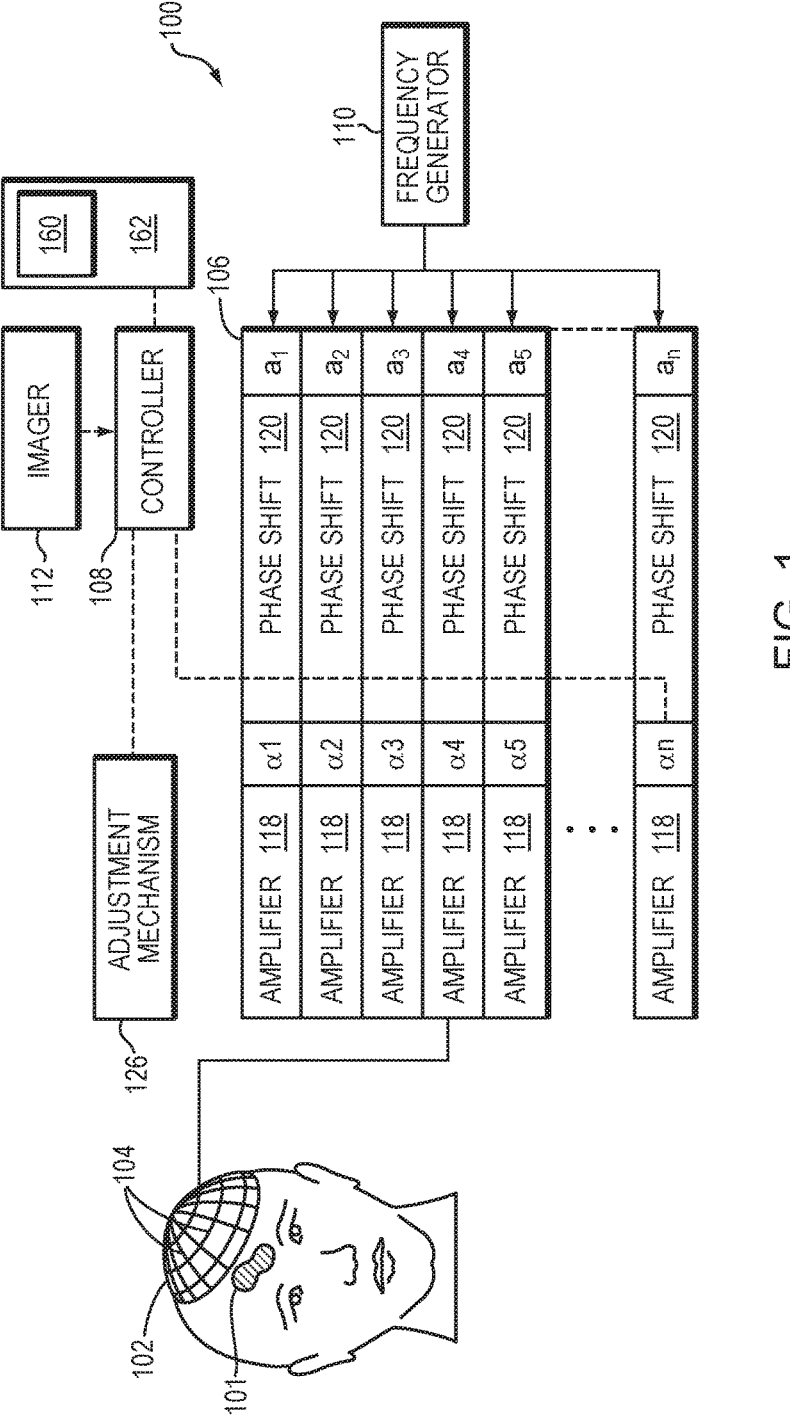
FIG. 1 schematically depicts an exemplary ultrasound system in accordance with various embodiments of the present invention.

FIG. 1 illustrates an exemplary ultrasound system 100 for focusing ultrasound onto a target region 101 through the skull. One of ordinary skill in the art, however, will understand that the ultrasound system 100 described herein may be applied to any part of the human body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on or near (e.g., separated by a water-filled pad from) the surface of the skull or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase delay circuit 120; drive circuit drives one of the transducer elements 104. The beamformer 106 receives a radio frequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes, such that the transducer elements 104 collectively form a "phased array."

Figure 2:
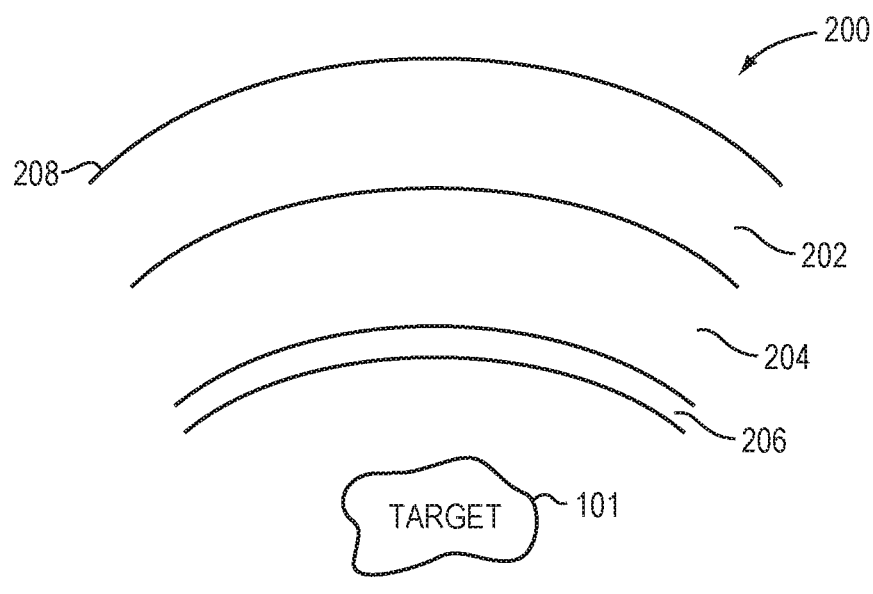
FIG. 2 schematically illustrates tissue layers of a human skull.

The acoustic waves/pulses transmitted from the transducer elements 104 form an acoustic energy beam. Typically, the transducer elements are driven so that the waves/pulses converge at a focal zone in the targeted tissue 101. Within the focal zone, the wave energy of the beam is (at least partially) absorbed by the tissue, thereby generating heat and raising the temperature of the tissue for therapeutic and/or diagnostic purposes. For example, the tissue may be heated to a point where the cells are denatured and/or ablated. Additionally or alternatively, the beam or changes therein may create cavitation, interact with bubbles in the tissue (causing mechanical effects or acoustic emission) and/or stimulate or inhibit neurological activity. To effectively treat the target tissue, the acoustic energy beam must be precisely focused to the target location 101 to avoid damage to healthy tissue surrounding the target region. With reference to FIG. 2, a typical human skull 200 is inhomogeneous and has multiple tissue layers, including an external layer 202, a bone marrow layer 204, and an internal layer or cortex 206; each layer of the skull 202 may be highly irregular in shape, thickness and density, and unique to a patient. As a result, when the ultrasound waves/pulses emitted from the system 100 encounter the skull 200, beam scattering, absorption, reflection, and/or refraction may occur due to tissue inhomogeneity; this may result in beam aberrations, which may distort the focus and reduce the intensity, thus affecting treatment efficiency. Accordingly, it is desired to adjust parameters (e.g., the phase shifts $a_1$-$a_n$ and/or amplification or attenuation factors $\alpha_1$-$\alpha_n$) of the drive signals associated with the transducer elements so as to compensate for the acoustic aberrations and thereby improve focusing properties at the target region 101.

Generally, the amplification factors and phase shifts may be computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, to determine a baseline set of the parameters (e.g., frequencies, phase shifts and/or amplification factors) of the transducer elements 104. The controller 108 may determine the parameters based on information about the characteristics (e.g., structure, thickness, density, etc.) of the skull and their effects on propagation of acoustic energy. Referring again to FIG. 1, in one embodiment, such information is obtained from an imager 112, which may be a magnetic resonance (MR) imaging device, a computer tomography (CT) device, a positron emission tomography (PET) device, a single-photon emission computed tomography (SPECT) device, or an ultrasonography device. Image acquisition may be three-dimensional (3D) or, alternatively, the imager 112 may provide a set of two-dimensional (2D) images suitable for reconstructing a three-dimensional image of the target region 101 and/or other regions (e.g., the region surrounding the target 101, the region in the pass zone located between the transducer and the target, or another target region). Image-manipulation functionality may be implemented in the imager 112, in the controller 108, or in a separate device. The amplification factors and phase shifts may be computed using the controller 108, which may provide the relevant computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of intervening tissues located between the transducer 102 and the target 101 (e.g., the pass zone) and their effects on propagation of acoustic energy.

In some embodiments, the ultrasound treatment involves an acoustic reflector (e.g., microbubbles). For example, microbubbles may be generated by acoustic energy and/or introduced by systemic injection for autofocusing. Ultrasound waves transmitted from all (or at least some) transducer elements 104 are reflected by the reflector; the reflection signals may be detected by the acoustic-signal sensor and/or the transducer elements 104. The measured signals may then be provided to the controller 108 to obtain information, such as the amplitudes and/or phases, associated with the reflections; these may be compared to the amplitudes and/or phases associated with the transmitted ultrasound waves from the transducer elements 104. Based on the deviations therebetween, the drive signals of the transducer elements 104 may be adjusted so as to compensate for the deviations, thereby improving the focusing properties. In some embodiments, this autofocusing procedure is iteratively performed until optimal focusing properties are achieved. Approaches for autofocusing an ultrasound beam at the target region are provided, for example, in PCT Publication Nos. WO 2018/020315 and WO 2020/128615; approaches to generating the microbubbles and/or introducing the microbubbles to the target region 101 are provided, for example, in PCT Publication Nos. WO 2018/020315, WO 2019/116107, WO 2019/058171, WO 2019/116097, WO 2019/002947, and WO 2019/116095, and U.S. Patent Publication Nos. 2019/0083065 and 2019/0178851. The entire contents of the foregoing applications are incorporated herein by reference.

In various embodiments, with reference to FIGS. 1 and 2, the adjustment mechanism 126 may include an autofocusing correction database 160 relating anatomic features identified in images created by the imager 112 to corrections to one or more ultrasound parameters such as frequency, amplitude, and/or phase. The features may include measurements of thickness and/or density of the layers 202, 204, 206, and other intervening tissue layers (estimated from automated analysis of CT or MR images), as well as the angle of the beam output of a transducer element relative to the surface 208 of the patient's skull (with the beam extending from the transducer element to the desired focus location). Approaches for determining the beam-skull angle are provided, for example, in U.S. Pat. Nos. 8,617,073 and 10,456, 603, the entire contents of which are incorporated herein by reference.

These features are utilized by the adjustment mechanism 126 to alter the baseline ultrasound parameters based on a trained predictor. In practice, the adjustment mechanism 126 may implement the predictor directly, e.g., as a regression module operative as described below; based on the feature values, the regression module computes appropriate adjustments to one or more ultrasound parameters associated with one or more transducer elements based on its prior training. In other implementations, the relationship between features and corresponding ultrasound parameters may be stored as a database with entries specific to each transducer element. These entries are obtained by providing a trained predictor with a range of inputs—in particular, a sufficient range to cover scenarios likely to be encountered across patients and a sufficient number to facilitate interpolation between database entries where one or more of the input feature values lie between stored values. Appropriate corrections are obtained by lookup (and, as necessary, interpolation) based on feature values, at least some of which are specific to transducer elements 104 (based on their individual geometric relationships to the target 101 and/or skull 200). It should be noted that, more generally, the sonication signal can be wrapped by a smoothing window (e.g., a Hamming window) to improve signal quality.

More specifically, the predictor may be used to provide initial focusing corrections when the autofocusing procedure is initiated, and/or to be used for elements with missing measurements or measurements known to be incorrect, and/or for targeting at a different location. In the latter two cases, the predictor can be adjusted during treatment using current treatment measurements. For example, as described in PCT Publication No. WO 2019/234495 (the entire disclosure of which is hereby incorporated by reference), ultrasound signals reflected from the acoustic reflector during the autofocusing procedure may be first analyzed to determine the quality (e.g., the signal-to-noise ratio, SNR) thereof. Based on the determined quality, the reflection signals are classified as (i) sufficient-quality signals that can be further analyzed to acquire corrections to the ultrasound parameter values for autofocusing or (ii) insufficient-quality signals (or incorrect signals or missing signals) that will not be utilized for autofocusing. The transducer elements receiving the sufficient-quality signals are classified as measuring elements, whereas the transducer elements receiving signals of insufficient quality are classified as non-measuring elements. Corrections to the ultrasound parameter values acquired using the measuring elements can be utilized to adjust the predictor. Based on the characteristics (e.g., thickness, density and beam-skull angle) associated with tissue intervening between the target region and the non-measuring elements, the adjusted predictor can generate corrections to parameter values associated with the non-measuring elements to create an optimal focus at the target. The determined correction values associated with the measuring and non-measuring elements can be stored along with their respective transducer elements in the database 160. In addition, the database can be used as the basis for synthetic data generation, i.e., generating data to train a predictor that may be used for autofocusing or other diagnostic or treatment purposes.

In some circumstances, the target region may span a large volume that cannot be fully treated in one treatment session (e.g., one focal zone) and/or there may be multiple target regions having discrete locations. It may thus be necessary to treat a second portion of the target region different from the first portion, and/or a second target region different from the first target region. In one implementation, the controller optionally adjusts the predictor using the corrections to ultrasound parameter values acquired in the autofocusing procedure and/or during treatment of the first target region (or the first portion of the target region). Based on the characteristics (e.g., thickness, density and beam-skull angle) associated with the intervening tissue located between the second target region (or the second portion of the target region) and the transducer elements, the adjusted predictor may generate corrections to parameter values associated with the transducer elements for treating the second target region (or the second portion of the target region).

Figure 3:
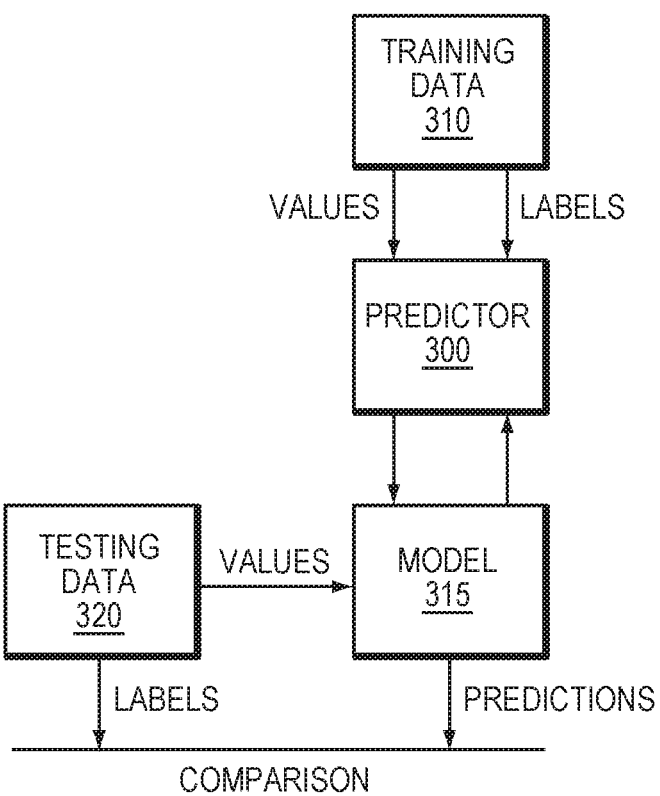
FIG. 3 schematically depicts a prediction module and a manner in which the prediction module is trained and used in accordance with various embodiments of the present invention.

FIG. 3 illustrates a prediction module 300 (implemented in the controller 108, a separate external controller or other computational entity or entities) and the manner in which it is trained and used. The prediction module may be based on any learning algorithm (or algorithms) suitable to the prediction task, e.g., a linear or nonlinear regression or Bayesian prediction, or may be a neural network. Organized in a highly interconnected brain-like fashion, neural networks can analyze and recognize patterns in a wide range of complex input. The learning algorithm may involve supervised or unsupervised learning.

FIG. 3 shows a supervised learning scenario in which the learning algorithm receives labeled training data 310. Each item of training data includes a vector of feature values and an associated label, i.e., the correct (or acceptable) parameter adjustment values. The predictor 300 assimilates the training data 310 and, based on its architecture, produces a model 315—a series of coefficients or "weights" in the case of simple linear regression or a more complex interconnected architecture of weights in the case of a neural network. Training may involve multiple passes of the training data 310 through the predictor 300, and once fully trained, the model 315 is tested with labeled testing data 320. Like the training data 310, each item of testing data 320 includes a vector of values and a label. The prediction made by the trained model 315 based on an item of testing data is compared to the label associated with that testing item. If, in the aggregate, the prediction accuracy is sufficiently high, the model 315 is considered fully trained; if not, the predictor may be supplied with additional training data and/or its architecture may be altered and the process of training and testing repeated until satisfactory predictive results are obtained.

In the present context, data relevant to two or more transducer elements are considered in a single data sample (i.e., feature vector). For example, consider a transducer of 1024 elements, where one of the samples is the pair {element #3, element #46}, and input data for each element corresponds only to three skull characteristics significant for shifting an element's beam—i.e., thickness, skull density and beam-skull angle—and the values of these characteristics are associated with the skull portion that the element's beam intersects. Then, the features of a data sample referring to the pair {element #3, element #46} would be (Thickness$_{el\ #3}$, Density$_{el\ #3}$, angle$_{el\ #3}$, Thickness$_{el\ #46}$, Density$_{el\ #46}$, angle$_{el\ #46}$), so that Density$_{el\ #3}$ and Density$_{el\ #46}$ refer to the density of the same skull, but at different locations. Hence, the input is of size 3 characteristics×2 elements=6. If the input takes the form of a 200×32 image, the input would be of size 200×32×2, with each 200×32 image corresponding to a different element. The label is the difference between the elements' measured parameter values (e.g., phases), and on inference, the output is the relative prediction; if relative value is expressed in terms of a difference, the prediction is $\varphi_{el\ #3}$-$\varphi_{el\ #46}$, where $\varphi_{el\ #i}$ denotes the phase shift associated with the transducer element i.

Now suppose that the total number of samples that describe the transducer is 10,000, where element combinations are selected according to one or more criteria, e.g., to ensure adequate redundancy (with each element appearing in more than one pair) so as to maximize prediction confidence. After inference, we then have 10,000 equations. For time delay, we have:

$$\begin{cases} \varphi_{el\#3} - \varphi_{el\#5} = P_{\{3,5\}} \\ \varphi_{el\#3} - \varphi_{el\#46} = P_{\{3,46\}} \\ \varphi_{el\#30} - \varphi_{el\#31} = P_{\{30,31\}} \\ \qquad \vdots \end{cases}$$

where $P_{\{i,j\}}$ is the model's prediction of the difference in the time delays of transducer elements i and j, i.e., known (geometrically determined) quantities, and the objective is to find the set $\varphi_{el\ #1}$, $\varphi_{el\ #2}$, ... $\varphi_{el\ #1024}$ that best satisfies the above difference equations according to an error metric (e.g., least-squares minimization), where the error associated with each equation may be weighted (based on skull transmission, model confidence, etc.)

Using the property that a constant phase bias does not affect the focusing quality, the equations can be represented as an overdetermined set of linear equations:

$$\begin{pmatrix} 1 & 0 & 0 & \dots & 0 & 0 \\ 1 & -1 & 0 & \dots & 0 & 0 \\ \vdots & \vdots & \vdots & \vdots & \vdots & \vdots \end{pmatrix} \begin{pmatrix} \varphi_{el\#1} \\ \varphi_{el\#2} \\ \vdots \end{pmatrix} = \begin{pmatrix} 0 \\ P_{\{1,2\}} \\ \vdots \end{pmatrix}$$

where the first row corresponds to setting a reference phase and each succeeding row to the equation predicting $P_{\{i,j\}}$ for one of the element pairs so that the matrix is 10,001×1024 and can be solved, for example, using ordinary least squares.

The case of wrapped phase shifts (as opposed to amplitude, time delay or full phase shift) introduces an additional difficulty due to the phase wrapping. The resulting set of 10,000 equations would be:

$$\begin{cases} \text{angle}(\exp(i(\varphi_{el\#3} - \varphi_{el\#5}))) = P_{\{3,5\}} \\ \text{angle}(\exp(i(\varphi_{el\#3} - \varphi_{el\#46}))) = P_{\{3,46\}} \\ \text{angle}(\exp(i(\varphi_{el\#30} - \varphi_{el\#31}))) = P_{\{30,31\}} \\ \qquad \vdots \end{cases}$$

where the phase shifts ($\varphi$) are confined to $[-\pi, \pi]$ and $P_{\{i,j\}}$ is the model's prediction of the difference of the wrapped phase shifts of elements i and j (usually re-wrapped to be confined also to $[-\pi, \pi]$). Again, $P_{\{i,j\}}$ are known quantities, and the objective is to find the set $\varphi_{el\ #1}$, $\varphi_{el\ #2}$, ... $\varphi_{el\ #1024}$ that best satisfies the above equations. The phase-wrapped equations can be written as:

$$\begin{pmatrix} 1 & 0 & 0 & \dots & 0 & 0 \\ 1 & -1 & 0 & \dots & 0 & 0 \\ \vdots & \vdots & \vdots & \vdots & \vdots & \vdots \end{pmatrix} \begin{pmatrix} \varphi_{el\#1} \\ \varphi_{el\#2} \\ \vdots \end{pmatrix} = \begin{pmatrix} 0 \\ P_{\{1,2\}} \\ \vdots \end{pmatrix} + 2\pi \begin{pmatrix} 0 \\ k_{\{1,2\}} \\ \vdots \end{pmatrix}$$

where the first row corresponds to setting a reference phase and the quantities $k_{\{i,j\}}$ are unknown. For brevity, we denote the above equation as $A \cdot \varphi = P_{\{\cdot\}} + 2\pi K_{\{\cdot\}}$, and refer to it as Eq. 1. One approach for solving this set of equations is as follows. First, set the phase-shift differences to the range $[0, 2\pi]$ instead of $[-\pi, \pi]$:

$$P'_{\{i,j\}} = \begin{cases} P_{\{i,j\}} & 0 \le P_{\{i,j\}} \le \pi \\ P_{\{i,j\}} + 2\pi & -\pi \le P_{\{i,j\}} \le 0 \end{cases}.$$

This change will have no effect on the solution. Eq. 1 can then be rewritten as:

$$(A \cdot \varphi)(\bmod\ 2\pi) = P'_{\{\cdot\}}(\bmod\ 2\pi)$$

The range $[0, 2\pi]$ can be discretized by defining a variable p as a large prime number and re-writing Eq. 1 as:

$$(A \cdot \varphi)(\bmod 2\pi) \cdot \frac{p}{2\pi} = \mathrm{round}\left(P'_{\{\cdot\}}(\bmod 2\pi) \cdot \frac{p}{2\pi}\right)$$

assuming p is high enough relative to model accuracy. Using the fact the number of $2\pi$ cycles in $\varphi$ is irrelevant to achieving optimal focusing, as well as the fact that all entries in the matrix A are either 1 or $-1$, Eq. 1 can be further rewritten as:

$$A \cdot \left(\varphi \cdot \frac{p}{2\pi}\right)(\bmod p) = \left(\mathrm{round}\left(P'_{\{\cdot\}} \cdot \frac{p}{2\pi}\right)\right)(\bmod p)$$

resulting in an overdetermined set of linear equations over a finite field, which can be solved over integers, for example, by Gaussian Elimination on multiple combinations of N equations, where N is the number of elements, and selecting best solution by best inter-solutions correspondence.

Another embodiment creates the wrapped phase shifts list from differences by solving an overdetermined set of quadratic equations:

$$\varphi_i - \varphi_j = P_{ij} \Rightarrow \begin{cases} \cos(\varphi_i - \varphi_j) = \cos(P_{ij}) \\ \sin(\varphi_i - \varphi_j) = \sin(P_{ij}) \\ \cos^2\varphi_i + \sin^2\varphi_i = 1 \\ \cos^2\varphi_j + \sin^2\varphi_j = 1 \end{cases} \Rightarrow$$

$$\begin{cases} \cos\varphi_i\cos\varphi_j + \sin\varphi_j\sin\varphi_i = \cos(P_{ij}) \\ \sin\varphi_i\cos\varphi_j + \cos\varphi_j\sin\varphi_i = \sin(P_{ij}) \\ \cos^2\varphi_i + \sin^2\varphi_i = 1 \\ \cos^2\varphi_j + \sin^2\varphi_j = 1 \end{cases} \Rightarrow \begin{cases} x_ix_j + y_iy_j = \cos(P_{ij}) \\ y_ix_j - x_iy_j = \sin(P_{ij}) \\ x_i^2 + y_i^2 = 1 \\ x_j^2 + y_j^2 = 1 \end{cases}$$

The objective function to be minimized is then:

$$f(x_1 \dots {}_n, y_1 \dots {}_n) = \Sigma_{eq.} x_ix_j + y_iy_j - \cos(P_{ij}) + y_ix_j - x_iy_i - \sin(P_{ij}) + x_i^2 + y_i^2 - 1 + x_j^2 + y_j^2 - 1,$$

where the sum can be weighted by transmission, confidence, etc. and its gradients can be calculated for using gradient descent:

$$\nabla f = \sum_{i=valid\ el} \frac{\partial f}{\partial x_i}\hat{x}_i + \frac{\partial f}{\partial y_i}\hat{y}_i$$

$$\frac{\partial f}{\partial x_i} = \sum_{eq.} x_j - y_j + 2x_i$$

$$\frac{\partial f}{\partial y_i} = \sum_{eq.} y_j + x_j + 2y_i$$

$$\vdots$$

For amplitude, it is found that the ratio of the amplitudes of reflection signals received by pairs of transducer elements (rather than differences, as in phase measurements) provide best results for the ultimate objective of compensating for beam aberration.

Hence, for amplitude, we have:

$$\begin{cases} \varphi_{el\#3}/\varphi_{el\#5} = P_{\{3,5\}} \\ \varphi_{el\#3}/\varphi_{el\#46} = P_{\{3,46\}} \\ \varphi_{el\#30}/\varphi_{el\#31} = P_{\{30,31\}} \\ \vdots \end{cases}$$

Once again the equations can be represented as an over-determined set of linear equations:

$$\begin{pmatrix} 1 & 0 & 0 & \dots & 0 & 0 \\ 1 & -P_{\{1,2\}} & 0 & \dots & 0 & 0 \\ \vdots & \vdots & \vdots & \vdots & \vdots & \vdots \end{pmatrix} \begin{pmatrix} \varphi_{el\#1} \\ \varphi_{el\#2} \\ \vdots \end{pmatrix} = \begin{pmatrix} 1 \\ 0 \\ \vdots \end{pmatrix}$$

where the first row corresponds to setting a reference amplitude and each succeeding row to the equation predicting $P_{\{i,j\}}$ for one of the element pairs. The use of ratios eliminates errors resulting from bias, because once again a constant bias applied to all elements of the transducer has no effect on the focusing quality.

Predicting the phase is very similar to predicting time delay. Usually, the term "time delay" refers to the entire time (or phase) difference that the skull medium causes relative to a water medium, e.g., 10 radians in terms of phase. The term "phase shift" generally refers to the wrapped phase confined to the interval $[-\pi, \pi]$. It may be more difficult to achieve accurate time delay measurements than the wrapped phase shift.

Figure 4:
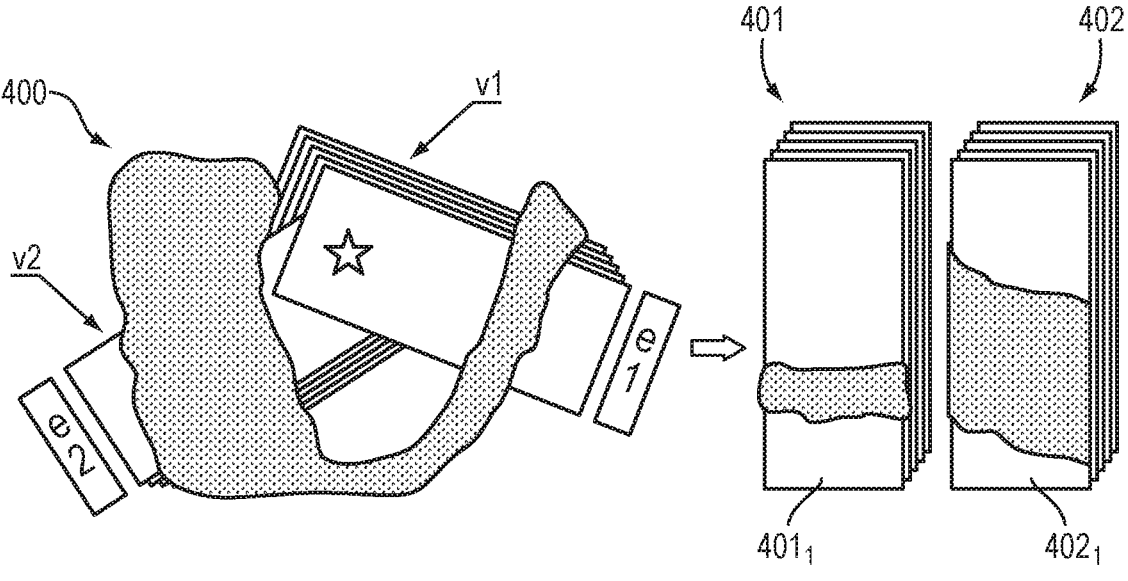
FIG. 4 schematically depicts imaged patches of the skull in accordance with various embodiments of the present invention.

In sum, the foregoing approaches replace what would otherwise be a k-length input vector for predictions based on single elements with 2 k-length vectors for pairs of elements (or n×k-length vectors for larger element groups). Other approaches to representing the data are possible, however. In one alternative, two sets of imaged patches of the skull medium can be combined, e.g., in a fourth dimension. For example, with reference to FIG. 4, the skull and brain medium that an element's beam passes through may be described by a 3D volume aligned with the beam, namely, the volume v1 corresponding to element e1 and the volume v2 corresponding to element e2. A first dimension extends along path from the element to the target, and the patch is extracted by interpolation of the skull CT image representatively indicated at 400; that is, the figure shows the CT image at the depth corresponding to the first layers of the volumes v1, v2. The skull patches 401, 402 correspond to v1 and v2, respectively, with the illustrated CT image layer 400 appearing on the first layer 401₁, 402₁ of the skull patches 401, 402. Succeeding layers of the skull patches 401, 402 would include image information from CT layers at depths corresponding to the patch layers along the third dimension. If each patch layer is 200×32 pixels and there are 32 layers, the dimensions of each patch volume are 200×32×32. Then, when a single data sample corresponding to a pair of elements is considered, both elements' skull media (as imaged by CT) are included in the sample input. Concatenating the patches along a fourth dimension produces a 200×32×32×2 input array.

Figure 5:
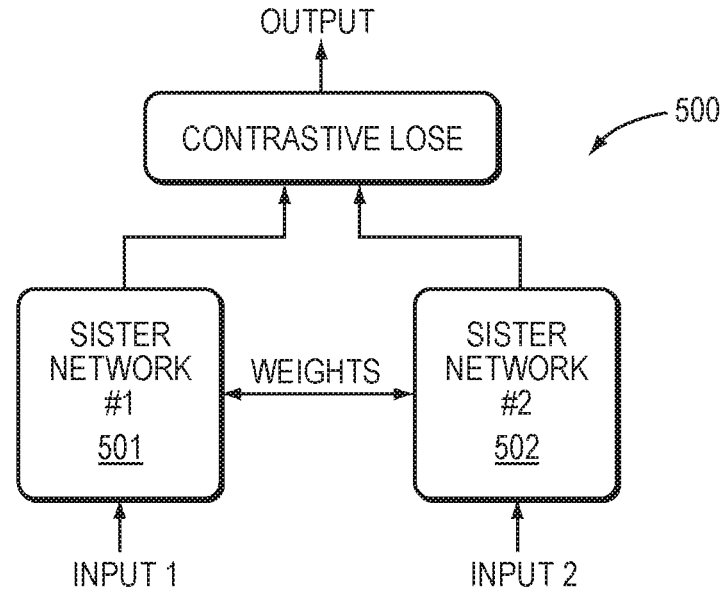
FIG. 5 schematically depicts a Siamese network for training a prediction model in accordance with various embodiments of the present invention.

In another approach, illustrated in FIG. 5, a Siamese network 500 is employed, each of the constituent neural networks 501, 502 receiving the input of a single element. That is, each element's skull patch/characteristics vector is an input to one of two identical neural networks 501, 502, which have the same architecture and share weights. Then, the outputs of the sister networks 501, 502 are combined to form a loss that depends only on the relative target values of the elements. This format can readily be extended to accommodate more than two elements in a sample by having a sister network for each sample element, and extending the Siamese network by including an additional neural network receiving the combined outputs of the multiple sister networks before loss evaluation.

In another embodiment using more than two elements, the features are a combination of their skull characteristics. For example, suppose all samples are of equal size, each data sample combines values from three elements, and the input parameters are thickness, density, and angle. Then if one of the samples consists of elements 3, 46, and 15, the features might be $$(\text{Thickness}_{el\ \#3}, \text{Density}_{el\ \#3}, \text{angle}_{el\ \#3}, \text{Thickness}_{el\ \#46}, \\ \text{Density}_{el\ \#46}, \text{angle}_{el\ \#46}, \text{Thickness}_{el\ \#15}, \text{Density}_{el} \\ {}_{\#15}, \text{angle}_{el\ \#15})$$

or concatenated volumes of size 200×32×32×3. The output may be a vector of relative values (e.g., the second and third relative to the first) and the loss might be a pressure-like score of the prediction vs. true values, weighted by a factor such as amplitude or difficulty of prediction.

$$\text{loss} = \sum_{el=1}^{3} A_{el} \cdot \exp\left(\varphi_{el}^{predicted} - \varphi_{el}^{true}\right)$$

Now suppose that the samples are of varying sizes. For example, transducer elements can be grouped or the transducer divided into sections encompassing multiple elements. To illustrate, the transducer may be divided into 16 zones or sections, each encompassing 64 neighboring elements. Each of these sections may have a different number of elements eligible for use in a particular procedure and which, therefore, can validly be considered in the dataset. A sample generation network may be used to partition the transducer into groups of eligible elements. For example, a recurrent or graph neural network may be used to model these sections and their differing numbers of valid elements. Alternatively, the entire transducer may be represented as a graph with the objective of optimizing both sample generation and label learning. For example, a sample-generating neural network may be initiated by causing it to perform random walks (possibly with constraints) of different numbers of steps and step sizes. The output of this network is used in the selection of elements in each data sample that is used as input to a graph neural network that learns the labels (as relative values) and returns the prediction and the prediction confidence level. These values may also be used in the estimation of the loss for the sample-generation model, along with the constraint that providing the generated samples with true labels would result in perfect focusing (e.g. by using all elements and forcing redundancy).

Another approach may use an unsupervised learning for detecting skull behavior. For example, in a treatment where autofocusing procedure was performed for part of the transducer, the learned behavior may be used to find the acoustic parameter for the elements with missing measurements, e.g., cluster analysis may be used by filling all elements with missing measurements in a cluster with median phase of the measured elements in that cluster.

Referring again to FIG. 1, in various embodiments, the determined ultrasound parameter corrections (including amplitudes, time delays and/or phase shifts) using the predictor described above and/or the appropriate pattern of element activations and deactivations for a particular procedure and patient anatomy are stored along with their respective transducer elements in the database 160 in memory 162 accessible by the adjustment mechanism 126 and/or the controller 108. In one implementation, the database stores the transducer elements and their corresponding parameter corrections resulting from the skull in a table whose entries are populated using the predictor described above. The memory may include or consist essentially of one or more volatile or non-volatile storage devices, e.g., random-access memory (RAM) devices such as DRAM, SRAM, etc., read-only memory (ROM) devices, magnetic disks, optical disks, flash memory devices, and/or other solid-state memory devices. All or a portion of the memory may be located remotely from the ultrasound system 100 and/or the imager 112, e.g., as one or more storage devices connected to ultrasound system 100 and/or the imager 112 via a network (e.g., Ethernet, WiFi, a cellular telephone network, the Internet, or any local- or wide-area network or combination of networks capable of supporting data transfer and communication). As utilized herein, the term "storage" broadly connotes any form of digital storage, e.g., optical storage, magnetic storage, semiconductor storage, etc.

In other embodiments, the predictor is part of (i.e., stored in memory 162 accessible to) the adjustment mechanism 126. For example, prior to treatment, the phases and/or amplitudes of reflection signals may be sensed by the transducer elements that will be used in the treatment procedure and input vectors created from (i) differences or ratios among sensed signals as described above, (ii) geometric parameters (e.g., angle) specific to each transducer element, and (iii) anatomic features (thickness, density) obtained by CT, MR, or other imaging modality. Each input vector is processed by the trained neural network, which outputs the correction values for the associated transducer element.

In one embodiment, the controller 108 implements a physical model to predict treatment effects (e.g., the real-time temperature) at the target region 101 and/or non-target region using tissue characteristics (e.g., the energy absorption coefficient) thereof and ultrasound parameter values (e.g., phases, amplitudes, etc.) stored in the database 160. In addition, the physical model may predict the real-time temperature at the focal zone (which may or may not coincide with the target region) and/or the shape of the focal zone. Based on the predicted treatment effects at the target/non-target region, the real-time temperature at the focal zone and/or the shape of the focal zone, the controller 108 may determine patient suitability for ultrasound treatment (e.g., the treatment success rate) using, for example, the physical model. In various embodiments, the tissue characteristics of the target and pass zone regions are acquired using the imager 112. For example, based on the acquired images, a tissue model characterizing the material characteristics of the target and pass zone regions may be established. The tissue model may take the form of a 3D table of cells corresponding to the voxels representing the target tissue; the cells have attributes whose values represent characteristics of the tissue, such as the absorption coefficient, that are relevant to the energy absorption. The voxels are obtained tomographically by the imaging device and the type of tissue that each voxel represents can be determined automatically by conventional tissue-analysis software. Using the determined tissue types and a lookup table of tissue parameters (e.g., absorption coefficient by type of tissue), the cells of the tissue model may be populated. During an autofocusing procedure, the measurements can be used to optimize tissue characteristics (which depend on the specific patient and the imager 112 employed) in the physical model which, in turn, may be used to target a new location or for missing measurements. Further detail regarding creation of a tissue model that identifies the energy absorption coefficient, heat sensitivity and/or thermal energy tolerance of various tissues may be found in U.S. Patent Publication No. 2012/0029396, the entire disclosure of which is hereby incorporated by reference.

Figure 6A:
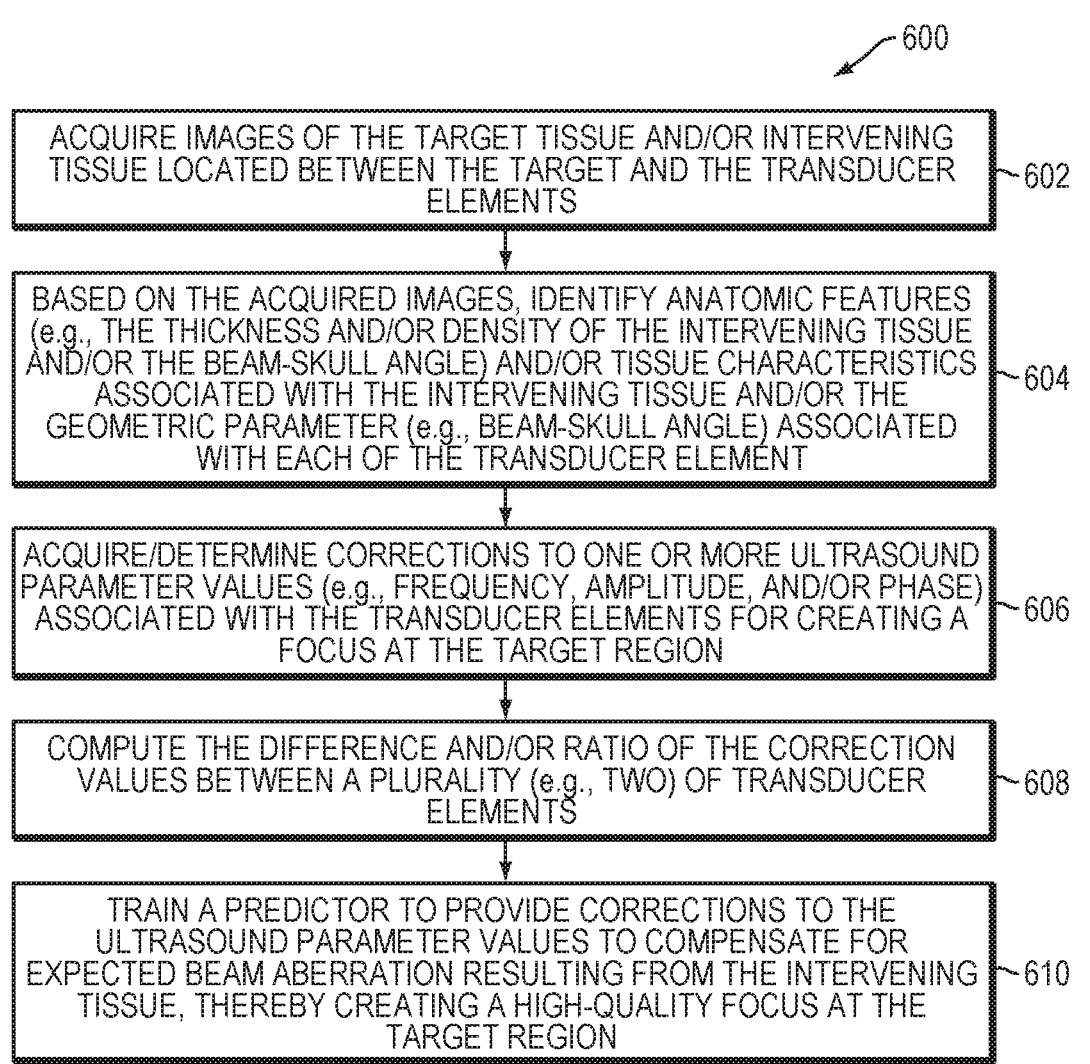
FIG. 6A is a flow chart illustrating an exemplary approach for training a prediction model to generate corrections to ultrasound parameter values associated with the transducer elements in accordance with various embodiments of the present invention.

FIG. 6A illustrates an exemplary approach 600 for training a predictor to generate corrections to ultrasound parameter values associated with the transducer elements. These parameter values facilitate compensation for expected beam aberration caused by the tissue intervening between the target region and the transducer elements in accordance herewith. In a first step 602, the imager 112 is activated to acquire images of the target tissue and/or intervening tissue. Based thereon, the controller 108 identifies numeric quantities characterizing the intervening tissue and/or target tissue (e.g., anatomic features such as thickness and/or density, and/or tissue characteristics such as the energy absorption coefficient) and/or a geometric parameter (e.g., beam-skull angle) associated with each of the transducer elements (in a second step 604). In one embodiment, it is necessary to register coordinate systems in different imaging modalities (e.g., ultrasound imaging, MRI imaging and/or CT imaging) in order to compute the beam-skull angle associated with each element. Exemplary registration approaches are provided, for example, in U.S. Pat. No. 9,934,570, the entire disclosures of which are hereby incorporated by reference. In addition, the controller may acquire/determine one or more correction values for the ultrasound parameters (e.g., frequency, amplitude, and/or phase) associated with the transducer elements to compensate for aberrations resulting from the intervening tissue having the identified anatomic features so as to create an optimal focus at the target region (in a third step 606). The correction values may be acquired/determined based on, for example, a retrospective study of previously performed ultrasound procedures. Further, the controller may compute the difference and/or ratio of the correction values between a plurality of (e.g., two) transducer elements (in a fourth step 608). The anatomic features identified in step 604 and the difference and/or ratio of the ultrasound parameter values determined in step 608 are then provided as training data to train a predictor that estimates ultrasound correction values from anatomic features (in a fourth step 610). The training may be based on any suitable learning algorithm and may involve supervised or unsupervised learning.

Once the predictor is trained, the controller 108 may implement the trained predictor to determine the optimal settings of the transducer elements, thereby creating optimal treatment effects at a target region of a patient during a therapeutic or diagnostic procedure. Referring to FIG. 6B, in a first step 652, the controller 108 may implement the predictor that has been trained to generate corrections to the ultrasound parameter values. In a second step 654, the controller 108 may provide, to the predictor, multiple input vectors, each including numeric quantities characterizing tissue intervening between the target region of the patient and the transducer elements to be activated during a treatment session. The numeric quantities may include anatomic features (e.g., thickness and/or density) and/or tissue characteristics associated with the target and/or intervening tissue and/or a geometric parameter (e.g., beam-skull angle) associated with each of the transducer element. Again, the numeric quantities may be obtained from images acquired using the imager 112. Based on the input vectors, the predictor may generate, as an output, correction values associated with the active transducer elements for creating an optimal focus at the target region (in a step 656). The controller 108 may then activate the transducer elements based on the corresponding correction values to initiate an autofocusing procedure (in a step 658). Subsequently, the controller 108 may cause the target region to be treated by operating the transducer elements using the ultrasound parameter values determined in the autofocusing procedure (in a step 660). The active transducer elements may include all elements of the transducer array. Alternatively, the active transducer elements may include only some of the elements in the transducer array. For example, based on the reflection signals received during the autofocusing procedure, the controller 108 may determine whether there are missing and/or incorrect measurements associated with one or more transducer elements in the autofocusing procedure (in a step 662). If so, the active transducer elements include only the elements that do not have missing and/or incorrect measurements. In some embodiments, the controller 108 optionally adjusts the predictor using the corrections to the ultrasound parameter values acquired in the autofocusing procedure (in a step 664). In addition, the controller may provide, to the adjusted predictor, multiple input vectors each including numeric quantities characterizing tissue intervening between the target region and the transducer elements having missing/incorrect measurements (in a step 666). Subsequently, the adjusted predictor may generate corrections to parameter values associated with the transducer elements having missing/incorrect measurements; and the controller may activate these transducer elements using the newly generated correction values. In some embodiments, the controller 108 further determines whether it is necessary to treat a second portion of the target region (e.g., when the target region spans a large volume that cannot be fully treated in step 660) and/or a second target region (e.g., when first and second target regions have discrete locations) (in an optional step 668). If so, the controller 108 may optionally adjust the predictor using the corrections to ultrasound parameter values acquired in the autofocusing procedure (performed in step 658) and/or during treatment of the target region (or the portion of the target region) (performed in step 660) (in a step 670). In addition, the controller may provide, to the adjusted predictor, multiple input vectors each including numeric quantities characterizing tissue intervening between the new target region (or the new portion of the target region) and the transducer elements (in a step 672). Subsequently, the adjusted predictor may generate corrections to parameter values associated with the transducer elements for treating the new target region (or the new portion of the target region); and the controller may activate the transducer elements based on the corresponding correction values.

In general, functionality implementing the predictor as described above, measuring quantities constituting an input vector or facilitating database lookup, training the predictor, providing an input to the trained predictor, receiving an output from the predictor, performing the autofocusing procedure, and adjusting the ultrasound parameter values during the ultrasound procedure, whether integrated within a controller of the imager and/or an ultrasound system or provided by a separate external controller, may be structured in one or more modules implemented in hardware, software, or a combination of both. For embodiments in which the functions are provided as one or more software programs, the programs may be written in any of a number of high level languages such as PYTHON, JAVA, C, C++, C#, BASIC, various scripting languages, and/or HTML. For neural networks, machine-learning libraries or frameworks such as TENSORFLOW, PYTORCH, THEANO, or CAFFE may be straightforwardly employed. Additionally, the software can be implemented in an assembly language directed to the microprocessor resident on a target computer (e.g., the controller); for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules. Moreover, the terms "prediction module" and "predictor" are used herein interchangeably.

Certain embodiments of the present invention are described above. It is, however, expressly noted that the present invention is not limited to those embodiments; rather, additions and modifications to what is expressly described herein are also included within the scope of the invention.

What is claimed is:

1. A system for delivering ultrasound energy to a target region during a therapeutic or diagnostic procedure, the system comprising:
an ultrasound transducer comprising a plurality of transducer elements, at least some of the transducer elements being designated as active during the therapeutic or diagnostic procedure;
an adjustment mechanism comprising a machine-learning model that has been trained on input vectors;
wherein the input vectors are constructed from at least one of a difference or a ratio of parameter values between a plurality of the transducer elements, the adjustment mechanism being configured (i) to receive numeric quantities characterizing tissue intervening between the active transducer elements and the target region and (ii) to generate, based on the input vectors and for each of the active transducer elements, at least one parameter value to compensate for expected beam aberration; and
a controller configured to activate the active transducer elements in accordance with the corresponding parameter values so as to generate an optimized focal zone at the target region during the therapeutic or diagnostic procedure.

2. The system of claim 1, wherein the machine-learning model is a neural network.

3. The system of claim 2, wherein the neural network is trained on input vectors each comprising parameters associated with a pair of the transducer elements.

4. The system of claim 1, wherein the adjustment mechanism comprises a lookup table of adjustment values generated by a machine-learning algorithm.

5. The system of claim 4, wherein the machine-learning algorithm is a neural network trained on input vectors each comprising parameters associated with more than two transducer elements.

6. The system of claim 1, wherein the numeric quantities comprise tissue density and thickness.

7. The system of claim 1, wherein the adjustment mechanism is further configured to generate the at least one parameter value based at least in part on at least one geometric parameter associated with the associated transducer element.

8. The system of claim 7, wherein the at least one geometric parameter is an angle with respect to a surface of a skull between the associated transducer element and the target region.

9. The system of claim 1, wherein the generated at least one parameter value specifies a correction to at least one of amplitude, phase, frequency, duty cycle, sonication pattern or time delay.

10. The system of claim 1, wherein the target region comprises a plurality of portions and the generated optimized focal zone is at a first portion of the target region, the controller being further configured to predict at least one of (i) a real-time temperature at a second portion, different from the first portion, of the target region, or a non-target region, (ii) a real-time temperature at the focal zone, (iii) a focal spot shape, or (iv) treatment success using a physical model.

11. The system of claim 1, wherein the controller is further configured to:
cause the active transducer elements to (i) transmit ultrasound waves to the target region and (ii) measure the reflections of the ultrasound waves from the target region;
based on the measurements, classify each of the active transducer elements as a measuring transducer element or a non-measuring transducer element; and
update the adjustment mechanism based at least in part on the measurements provided by the measuring transducer elements.

12. The system of claim 11, wherein the updated adjustment mechanism is configured (i) to receive numeric quantities characterizing tissue intervening between the non-measuring transducer elements and the target region and (ii) based thereon, to generate, for each of the non-measuring transducer elements, at least one updated parameter value to compensate for expected beam aberration.

13. The system of claim 12, wherein the controller is further configured to activate the non-measuring transducer elements in accordance with the corresponding updated parameter values.

14. The system of claim 1, wherein the controller is further configured to:
cause the active transducer elements to (i) transmit ultrasound waves to the target region and (ii) measure reflections of the ultrasound waves from the target region; and update the adjustment mechanism based at least in part on the measurements.

15. The system of claim 14, wherein the updated adjustment mechanism is configured (i) to receive numeric quantities characterizing tissue intervening between the active transducer elements and a secondary target region, different from the target region, and (ii) based thereon, to generate, for each of the active transducer elements, at least one updated parameter value to compensate for expected beam aberration.

16. The system of claim 15, wherein the controller is further configured to activate the active transducer elements in accordance with the corresponding updated parameter values so as to generate an optimized focal zone at the secondary target region.

17. The system of claim 1, wherein the input vectors are constructed from one or more transformations of at least one of a difference and/or ratio of parameter values between the active transducer elements.

18. A method for delivering ultrasound energy to a target region during a therapeutic or diagnostic procedure using an ultrasound transducer comprising a plurality of transducer elements, at least some of the transducer elements being designated as active during the therapeutic or diagnostic procedure, the method comprising:
  providing an adjustment mechanism comprising a machine-learning model that has been trained on input vectors, wherein the input vectors are constructed from at least one of a difference or a ratio of parameter values between a plurality of the transducer elements;
  receiving, via the adjustment mechanism, numeric quantities characterizing tissue intervening between the active transducer elements and the target region;
  generating, via the adjustment mechanism, based on the input vectors and for each of the active transducer elements, at least one parameter value to compensate for expected beam aberration; and
  activating, using a controller, the active transducer elements in accordance with the corresponding parameter values so as to generate an optimized focal zone at the target region during the therapeutic or diagnostic procedure.

19. The method of claim 18, wherein the machine-learning model is a neural network.

20. The method of claim 19, wherein the neural network is trained on input vectors each comprising parameters associated with a pair of the transducer elements.

21. The method of claim 18, wherein the adjustment mechanism comprises a lookup table of adjustment values generated by a machine-learning algorithm.

22. The method of claim 21, wherein the machine-learning algorithm is a neural network trained on input vectors each comprising parameters associated with more than two transducer elements.

23. The method of claim 18, wherein the numeric quantities comprise tissue density and thickness.

24. The method of claim 18, wherein the method further comprises generating, via the adjustment mechanism, the at least one parameter value based at least in part on at least one geometric parameter associated with the associated transducer element.

25. The method of claim 24, wherein the at least one geometric parameter is an angle with respect to a surface of a skull between the associated transducer element and the target region.

26. The method of claim 18, wherein the generated at least one parameter value specifies a correction to at least one of amplitude, phase, frequency, duty cycle, sonication pattern or time delay.

27. The method of claim 18, wherein the target region comprises a plurality of portions and the generated optimized focal zone is at a first portion of the target region, and the method further comprises predicting, using the controller, at least one of (i) a real-time temperature at a second portion, different from the first portion, of the target region, or a non- target region, (ii) a real-time temperature at the focal zone, (iii) a focal spot shape, or (iv) treatment success using a physical model.

28. The method of claim 18, further comprising:
  causing, using the controller, the active transducer elements to (i) transmit ultrasound waves to the target region and (ii) measure the reflections of the ultrasound waves from the target region;
  based on the measurements, classifying, using the controller, each of the active transducer elements as a measuring transducer element or a non-measuring transducer element; and
  updating, using the controller, the adjustment mechanism based at least in part on the measurements provided by the measuring transducer elements.

29. The method of claim 28, wherein the method further comprises:
  receiving, at the updated adjustment mechanism, numeric quantities characterizing tissue intervening between the non-measuring transducer elements and the target region and
  based thereon, generating for each of the non-measuring transducer elements, using the updated adjustment mechanism, at least one updated parameter value to compensate for expected beam aberration.

30. The method of claim 29, further comprising:
  activating, using the controller, the non-measuring transducer elements in accordance with the corresponding updated parameter values.

31. The method of claim 18, further comprising:
  causing the active transducer elements, using the controller, to (i) transmit ultrasound waves to the target region and (ii) measure reflections of the ultrasound waves from the target region; and
  updating, using the controller, the adjustment mechanism based at least in part on the measurements.

32. The method of claim 31, further comprising:
  receiving, at the updated adjustment mechanism, numeric quantities characterizing tissue intervening between the active transducer elements and a secondary target region, different from the target region; and
  based thereon, generating for each of the active transducer elements, using the updated adjustment mechanism, at least one updated parameter value to compensate for expected beam aberration.

33. The method of claim 32, further comprising activating, using the controller, the active transducer elements in accordance with the corresponding updated parameter values so as to generate an optimized focal zone at the secondary target region.

34. The method of claim 18, wherein the input vectors are constructed from one or more transformations of at least one of a difference and/or ratio of parameter values between the active transducer elements.

* * * * *